(12) United States Patent
Vidal et al.

(10) Patent No.: US 6,679,923 B2
(45) Date of Patent: *Jan. 20, 2004

(54) COMPOSITION FOR DYEING KERATIN FIBERS, COMPRISING A PYRAZOLINE-4,5-DIONE AND AN AROMATIC PRIMARY AMINE

(75) Inventors: Laurent Vidal, Paris (FR); Gérard Malle, Villiers sur Morin (FR); Mireille Maubru, Chatou (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/192,524

(22) Filed: Jul. 11, 2002

(65) Prior Publication Data

US 2002/0194685 A1 Dec. 26, 2002

Related U.S. Application Data

(63) Continuation of application No. 09/423,521, filed as application No. PCT/FR98/00619 on Mar. 26, 1998, now Pat. No. 6,464,732.

(30) Foreign Application Priority Data

May 13, 1997 (FR) .............................. 97 05843

(51) Int. Cl.[7] ................................................ A61K 7/13
(52) U.S. Cl. ....................... 8/407; 8/409; 8/410; 8/416; 8/421; 8/423; 8/573
(58) Field of Search ..................... 8/407, 409, 410, 8/416, 421, 423, 573

(56) References Cited

U.S. PATENT DOCUMENTS

| 3,617,167 A | 11/1971 | Berth et al. |
| 3,820,948 A | 6/1974 | Berth |
| 5,718,731 A | 2/1998 | Loewe et al. |
| 6,464,732 B1 * | 10/2002 | Vidal et al. |

FOREIGN PATENT DOCUMENTS

| DE | 43 14 317 | 11/1994 |
| DE | 43 14 318 | 11/1994 |
| DE | 43 17 855 | 12/1994 |
| DE | 43 18 742 | 12/1994 |
| DE | 43 35 623 | 4/1995 |
| DE | 43 35 625 | 4/1995 |
| DE | 43 35 626 | 4/1995 |
| DE | 43 35 627 | 4/1995 |
| DE | 43 35 628 | 4/1995 |
| DE | 44 09 143 | 9/1995 |
| DE | 44 22 603 | 1/1996 |
| EP | 0 359 465 | 3/1990 |
| EP | 0 497 697 | 8/1992 |
| EP | 0 502 783 | 9/1992 |
| EP | 0 502 784 | 9/1992 |
| FR | 1 488 169 | 7/1967 |
| WO | WO 93/19725 | 10/1993 |
| WO | WO 95/24886 | 9/1995 |
| WO | WO 97/35842 | 10/1997 |

OTHER PUBLICATIONS

English language Derwent Abstract of DE 43 14 317.
English language Derwent Abstract of DE 43 14 318.
English language Derwent Abstract of DE 43 17 855.
English language Derwent Abstract of DE 43 18 742.
English language Derwent Abstract of DE 43 35 623.
95/24886

* cited by examiner

Primary Examiner—Margaret Einsmann
(74) Attorney, Agent, or Firm—Finnegan, Henderson, Farabow, Garrett & Dunner, L.L.P.

(57) ABSTRACT

The invention concerns a composition for dyeing keratin fibers, in particular human keratin fibers such as hair comprising at least one pyrazolin-4,5-dione of formula (I) and at least one aromatic primary amine. Said composition enables the dyeing of keratin fibers without an oxidizing agent in shades which are strong, varied, resistant and less selective than those of prior art. The invention also concerns dyeing methods and devices using said composition.

(I)

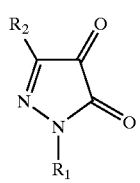

9 Claims, No Drawings

COMPOSITION FOR DYEING KERATIN FIBERS, COMPRISING A PYRAZOLINE-4,5-DIONE AND AN AROMATIC PRIMARY AMINE

This is a continuation of application Ser. No. 09/423,521 now U.S. Pat. No. 6,464,732 filed Nov. 10, 1999, which is a National Stage Application of International Application No. PCT/FR98/00619, filed Mar. 26, 1998, both of which are incorporated herein by reference.

The present invention relates to a composition for dyeing keratin fibres, in particular human keratin fibres such as the hair, comprising at least one pyrazoline-4,5-dione and at least one aromatic or heteroaromatic primary amine, and to dyeing processes and devices using this composition.

For the dyeing of keratin fibres, and in particular human keratin fibres such as the hair, it is known practice to use dye compositions containing oxidation dye precursors, generally known as oxidation bases, which are colourless or faintly coloured compounds which, when combined with oxidizing products, give rise to coloured compounds and dyes by means of an oxidative condensation process.

It is also known how to vary the shades obtained with these oxidation bases, by combining them with couplers or coloration modifiers. The variety of molecules used as regards the oxidation bases and couplers makes it possible to obtain a wide variety of colours. The colourations obtained are generally intense with good properties in terms of resistance over time (fastness) in the face of external agents (light, bad weather, washing, permanent-waving, perspiration, friction). However, the development of the colour requires the presence of an oxidizing agent, most generally aqueous hydrogen peroxide solution, the consequences of which are more or less pronounced deterioration of the state of the fibre.

It is also known practice to dye keratin fibres with direct dyes which are applied under mild conditions and which, consequently, generally respect the state of the fibre. However, the shades obtained with these direct dyes are not particularly intense and often need to be enhanced. In addition, their resistance to external agents is not as good, in particular their resistance to washing, and it is often considered to be insufficient.

To overcome these various drawbacks, it has already been proposed to dye the hair without an oxidizing agent, with dye compositions comprising either (a) 2,3-indolinedione, also known as "isatin" or one of its derivatives, or (b) a 1,2-ethanedione derivative, or (c) a 1,3-propanedione derivative, or (d) an indolinone derivative, with one or more aromatic amines and/or amino acids and/or oligopeptides and/or amino sugars and/or phenolic derivatives.

Such dye compositions have been described in the following documents:
  for 2,3-indolinedione and its derivatives: patents and patent applications U.S. Pat. No. 4,750,408, EP-0,359,465, EP-0,497,697, EP-0,502,783, EP-0,502,784, EP-0,634,923, EP-0,750,490, DE-4,314,317, DE-4,314,318, DE-4,409,143,
  for the 1,2-ethanedione derivatives: patent applications DE-4,317,855, DE-4,318,742, DE-4,335,625,
  for the 1,3-propanedione derivatives: patent applications DE-4,335,626, DE-4,335,627, DE-4,335,628,
  for the indolinone derivatives: patent application DE-4,335,623.

However, the colourations obtained using the said combinations are not always satisfactory, in particular as regards certain properties such as the sheen, the strength, the fastness and the selectivity. As regards selectivity, a good hair dye should be as homogeneous as possible from the root to the tip of the hair, in which case it is said to be unselective or relatively unselective.

However, hair colourations not comprising an oxidizing agent, such as direct colourations or the colourations obtained using the abovementioned combinations of isatin, 1,2-ethanedione, 1,3-propanediione or indolinone, generally have the drawback of being highly selective. There is thus a real need to have available hair dye compositions which contain no oxidizing agent, in order to respect the state of the fibre, and which give strong shades while being relatively unselective.

After considerable research conducted in this matter, the Applicant has now discovered, entirely surprisingly and unexpectedly, that varied shades which are both shiny, strong, fast and relatively unselective can be obtained by applying a dye composition containing at least one pyrazoline-4,5-dione of formula (I) and at least one aromatic or heteroaromatic amine of formula (II), which are defined below, to keratin fibres, in the absence of an oxidizing agent.

This discovery forms the basis of the present invention.

The present invention relates to a composition for dyeing keratin fibres, in particular human keratin fibres such as the hair, containing, in a medium which is suitable for dyeing, (i) at least one pyrazoline-4,5-dione of formula (I) and (ii) at least one aromatic or heteroaromatic amine of formula (II), which are defined below.

Another subject of the invention is a two-component composition for which, in a medium which is suitable for dyeing, one component contains at least one pyrazoline-4,5-dione of formula (I), the other component contains an aromatic or heteroaromatic amine of formula (II), formulae (I) and (II) being defined below, and which, being stored separately, are (i) mixed together at the time of use for application to the keratin fibres or (ii) applied sequentially to the said fibres.

A subject of the invention is also dyeing processes using these compositions.

Another subject of the invention relates to a multi-compartment device, or "kits", for dyeing keratin fibres, characterized in that it comprises at least two compartments, one of which contains a composition containing, in a medium which is suitable for dyeing, at least one pyrazoline-4,5-dione of formula (I), and the other contains a composition containing, in a medium which is suitable for dyeing, at least one aromatic or heteroaromatic amine of formula (II) which can react without an oxidizing agent with the pyrazoline-4,5-dione of formula (I) to form a dye (formulae (I) and (II) being defined below.)

However, other characteristics, aspects and advantages of the invention will emerge even more clearly on reading the description which follows, as well as the various concrete, but in no way limiting, examples intended to illustrate it.

(i) The pyrazoline-4,5-diones according to the present invention are compounds of formula (I) below:

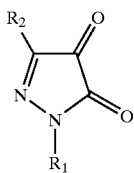

(I)

in which R₁ represents:
a hydrogen atom or a linear or branched $C_1-C_6$ alkyl radical optionally substituted with an OH, COOH, $C_1-C_4$ alkoxy, $C_1-C_4$ hydroxyalkyl or $C_1-C_4$ dialkylamino radical,
a radical:

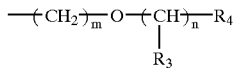

in which m=1, 2 or 3; n=1, 2 or 3; $R_3$=hydrogen or methyl; $R_4$=methyl, hydroxyl, linear or branched $C_1-C_5$ alkoxy or linear or branched $C_1-C_5$ hydroxyalkyl, a radical $-(CH_2)_p-O-R_5$ in which p=1 or 2 and $R_5$ represents a substituted or unsubstituted phenyl radical, a radical $-(CH_2)_q-R_6$ in which q=1 or 2, and $R_6$ represents a thienyl, furyl, pyridyl or piperidyl radical or a phenyl radical which is unsubstituted or substituted with a maximum of 2 radicals chosen from methyl, trifluoromethyl, sulphonyl and methoxy radicals, a phenyl radical which is unsubstituted or substituted with one to five radicals chosen from: —COOH, —CH₂COOH, —NO₂, —OH, —SO₃H, —CH₂OH, —OCF₃, —CF₃, —SO₂CH₃, —SO₂NH₂, —SO₂NHC₂H₅, —SO₂NHCH₂CH₂OH, —CON(CH₃)₂, —CON(C₂H₅)₂, —CH₂N(CH₃)₂, —CH₂N(C₂H₅)₂, —NHCOCH₃, —NHCOC₂H₅, a halogen atom such as Cl, Br or F, a linear or branched $C_1-C_3$ alkyl radical, a radical —Z—R₇ in which Z denotes O or S and R₇ denotes H, and a linear or branched $C_1-C_3$ alkyl radical, a benzyl radical which is unsubstituted or substituted with a —COOH, —OCH₃ or —SO₃H radical, a pyridyl, pyrimidinyl, pyrazinyl, thiazinyl, benzothiazolyl, benzimidazolyl, thienyl, imidazolyl, thiazolyl, 1,2,4-triazolyl, indazolyl, indolyl, quinolyl or isoquinolyl radical, and R₂ represents:
a hydrogen atom or a linear or branched $C_1-C_6$ alkyl radical optionally substituted with a hydroxyl or $C_1-C_4$ alkoxy radical,
a phenyl radical which is unsubstituted or substituted with a halogen atom (Cl, Br or F), a nitro radical or a trifluoromethyl radical,
a phenyl radical substituted with a maximum of 3 radicals chosen from $C_1-C_4$ alkyl, $C_1-C_4$ alkoxy, $C_1-C_4$ dialkylamino and $C_1-C_2$ alkylthio radicals,
a radical $-(CH_2)_r-R_8$ in which r=1, 2 or 3 and $R_8$ denotes an —SO₃H, $C_1-C_2$ alkylthio or benzylthio radical, a methoxycarbonyl or ethoxycarbonyl radical, a phenyl radical optionally substituted with a halogen atom (Cl, Br or F), a $C_1-C_3$ alkyl radical, a $C_1-C_3$ alkoxy radical or a $C_1-C_4$ dialkylamino or $C_1-C_2$ alkylthio radical,
a $C_1-C_4$ alkoxy radical; a phenoxy radical optionally substituted with one or more halogen atoms (Cl, Br or F); a trifluoromethyl, acetamido, carboxyl, methoxycarbonyl or ethoxycarbonyl radical; a thienyl, furyl, pyridyl or pyrazolyl radical, it being understood that when R₂ denotes an alkyl or phenyl radical, R₂ can be linked to the carbon atom of the pyrazoline ring via a hetero atom denoting O, N or S, and the cosmetically acceptable salts of these compounds.

Among the pyrazoline-4,5-diones of formula (I) which can be used in the dye compositions according to the present invention, the ones more particularly preferred are the compounds of formula (I) for which, R₁ denotes:
a hydrogen atom,
a linear or branched $C_1-C_4$ alkyl radical optionally substituted with a hydroxyl or $C_1-C_2$ alkoxy radical,
a radical $-(CH_2)_q-R_6$ in which q=1 or 2, and $R_6$ denotes a phenyl radical optionally substituted with a methyl, trifluoromethyl or sulphonyl radical,
a phenyl radical optionally substituted with a $C_1-C_2$ alkyl radical, a $C_1-C_2$ alkoxy radical, an —SO₃H, —COOH, —OH, —CF₃ or —NO₂ radical or a halogen atom (Cl, Br or F), and those of formula (I) for which R₂ denotes:
a hydrogen atom,
a linear or branched $C_1-C_4$ alkyl radical optionally substituted with a hydroxyl or $C_1-C_2$ alkoxy radical,
a phenyl radical optionally substituted with a halogen atom (Cl, Br or F), a $C_1-C_4$ alkyl radical, a $C_{1-C2}$ alkoxy radical or a $C_1-C_2$ dialkylamino radical,
a $C_1-C_3$ alkoxy radical, a trifluoromethyl radical, an acetamido radical, a $C_1-C_2$ dialkylamino radical, a carboxyl radical, a methoxycarbonyl or ethoxycarbonyl radical or a furyl, thienyl, pyridyl or pyrazolyl radical.

Among the said pyrazoline-4,5-diones, mention may be made in particular of the following compounds:
3-methyl-1-phenylpyrazoline-4,5-dione; 1-phenylpyrazoline-4,5-dione; 3-tert-butyl-1-phenylpyrazoline-4,5-dione; 1,3-diphenylpyrazoline-4,5-dione; 1-phenyl-3-(4'-methylphenyl)pyrazoline-4,5-dione, 1-phenyl-3-(4'-methoxyphenyl)pyrazoline-4,5-dione; 1-phenyl-3-(4'-nitrophenyl)pyrazoline-4,5-dione; 3-methoxy-1-phenylpyrazoline-4,5-dione; 3-ethoxy-1-phenylpyrazoline-4,5-dione; 3-acetamido-1-phenylpyrazoline-4,5-dione; 3-carboxy-1-phenylpyrazoline-4,5-dione; 3-methoxycarbonyl-1-phenylpyrazoline-4,5-dione; 2'-furyl-1-phenylpyrazoline-4,5-dione; 1-phenyl-3-trifluoromethylpyrazoline-4,5-dione; 1-[(3'-trifluoromethyl)benzyl)]-3-methylpyrazoline-4,5-dione; 1-[(1'-phenyl)ethyl)]-3-methylpyrazoline-4,5-dione; 3-methylpyrazoline-4,5-dione; 1,3-dimethylpyrazoline-4,5-dione; 3-methyl-1-(4'-nitrophenyl)pyrazoline-4,5-dione; 3-methoxypyrazoline-4,5-dione; 3-ethoxypyrazoline-4,5-dione; 1-methylpyrazoline-4,5-dione; 1-methyl(-3-phenylpyrazoline-4,5-dione; 1-methyl-3-(4'-chlorophenyl)pyrazoline-4,5-dione; 1-methyl-3-(3'-methoxyphenyl)pyrazoline-4,5-dione; 1-methyl-3-(4'-methoxyphenyl)pyrazoline-4,5-dione; 1-methyl-3-(3'-nitrophenyl)pyrazoline-4,5-dione; 1-methyl-3-(4'-methylphenyl)pyrazoline-4,5-dione; 1-methyl-3-(2'-furyl)pyrazoline-4,5-dione; 1-methyl-3-methoxypyrazoline-4,5-dione; 3-ethoxy-1-methylpyrazoline-4,5-dione; 3-acetamido-1-methylpyrazoline-4,5-dione;

3-carboxy-1-methylpyrazoline-4,5-dione; 3-methoxycarbonyl-1-methylpyrazoline-4,5-dione; 1-methyl-3-trifluoromethylpyrazoline-4,5-dione; 1-methyl-3-tert-butylpyrazoline-4,5-dione; 1-ethylpyrazoline-4,5-dione; 1-ethyl-3-methyl-pyrazoline-4,5-dione; 1-ethyl-3-phenylpyrazoline-4,5-dione; 1-ethyl-3-(4'-chlorophenyl)pyrazoline-4,5-dione; 1-ethyl-3-(3'-methoxyphenyl)pyrazoline-4,5-dione; 1-ethyl-3-(4'-methoxyphenyl)pyrazoline-4,5-dione; 1-ethyl-3-(3'-nitrophenyl)pyrazoline-4,5-dione; 1-ethyl-3-(4'-methylphenyl)pyrazoline-4,5-dione; 1-ethyl-3-(2'-furyl)pyrazoline-4,5-dione; 1-ethyl-3-methoxypyrazoline-4,5-dione; 1-ethyl-3-ethoxypyrazoline-4,5-dione; 1-ethyl-3-acetamido-pyrazoline-4,5-dione; 1-ethyl-3-carboxypyrazoline-4,5-dione; 1-ethyl-3-methoxycarbonylpyrazoline-4,5-dione; 1-ethyl-3-trifluoromethylpyrazoline-4,5-dione; 1-ethyl-3-tert-butylpyrazoline-4,5-dione; 1-isopropylpyrazoline-4,5-dione; 1-isopropyl-3-methyl-pyrazoline-4,5-dione; 1-isopropyl-3-phenylpyrazoline-4,5-dione; 1-isopropyl-3-(4'-chlorophenyl)pyrazoline-4,5-dione; 1-isopropyl-3-(3'-methoxyphenyl)pyrazoline-4,5-dione; 1-isopropyl-3-(4'-methoxyphenyl)pyrazoline-4,5-dione; 1-isopropyl-3-(3'-nitrophenyl)pyrazoline-4,5-dione; 1-isopropyl-3-(4'-methylphenyl)pyrazoline-4,5-dione; 1-isopropyl-3-(2'-furyl)pyrazoline-4,5-dione; 1-isopropyl-3-methoxypyrazoline-4,5-dione; 1-isopropyl-3-ethoxypyrazoline-4,5-dione; 1-isopropyl-3-acetamidopyrazoline-4,5-dione; 1-isopropyl-3-carboxy-pyrazoline-4,5-dione; 1-isopropyl-3-methoxycarbonyl-pyrazoline-4,5-dione; 1-isopropyl-3-tert-butylpyrazoline-4,5-dione; 1-isopropyl-3-trifluoro-methylpyrazoline-4,5-dione; 1-tert-butylpyrazoline-4,5-dione; 1-tert-butyl-3-methylpyrazoline-4,5-dione; 1-tert-butyl-3-phenylpyrazoline-4,5-dione; 1-tert-butyl-3-(4'-chlorophenyl)pyrazoline-4,5-dione; 1-tert-butyl-3-(3'-methoxyphenyl)pyrazoline-4,5-dione; 1-tert-butyl-3-(4'-methoxyphenyl)pyrazoline-4,5-dione; 1-tert-butyl-3-(3'-nitrophenyl)pyrazoline-4,5-dione; 1-tert-butyl-3-(4'-methylphenyl)pyrazoline-4,5-dione; 1-tert-butyl-3-(2'-furyl)pyrazoline-4,5-dione; 1-tert-butyl-3-methoxypyrazoline-4,5-dione; 1-tert-butyl-3-acetamidopyrazoline-4,5-dione; 1-tert-butyl-3-carboxypyrazoline-4,5-dione; 1-tert-butyl-3-methoxycarbonylpyrazoline-4,5-dione; 1-tert-butyl-3-trifluoromethylpyrazoline-4,5-dione; 1,3-di-tert-butylpyrazoline-4,5-dione; 1-(4'-methylphenyl)-pyrazoline-4,5-dione; 1-(4'-methylphenyl)-3-methylpyrazoline-4,5-dione; 1-(4'-methylphenyl)-3-phenylpyrazoline-4,5-dione; 1-(4'-methylphenyl)-3-(4'-chlorophenyl)pyrazoline-4,5-dione; 1-(4'-methylphenyl)-3-(3'-methoxyphenyl)pyrazoline-4,5-dione; 1-(4'-methylphenyl)-3-(4'-methoxyphenyl)-pyrazoline-4,5-dione; 1-(4'-methylphenyl)-3-(3'-nitro-phenyl)pyrazoline-4,5-dione; 1-(4'-methylphenyl)-3-(4'-methylphenyl)pyrazoline-4,5-dione; 1-(4'-methylphenyl)-3-(2'-furyl)pyrazoline-4,5-dione; 1-(4'-methylphenyl)-3-(2'-thienyl)pyrazoline-4,5-dione; 1-(4'-methylphenyl)-3-(5'-pyrazolyl)pyrazoline-4,5-dione; 1-(4'-methylphenyl)-3-methoxypyrazoline-4,5-dione; 1-(4'-methylphenyl)-3-ethoxypyrazoline-4,5-dione; 1-(4'-methylphenyl)-3-dimethylamino-pyrazoline-4,5-dione; 1-(4'-methylphenyl)-3-diethylaminopyrazoline-4,5-dione; 1-(4'-methylphenyl)-3-acetamidopyrazoline-4,5-dione; 1-(4'-methylphenyl)-3-carboxypyrazoline-4,5-dione; 1-(4'-methylphenyl)-3-methoxycarbonylpyrazoline-4,5-dione; 1-(4'-methylphenyl)-3-ethoxycarbonyl-pyrazoline-4,5-dione; 1-benzylpyrazoline-4,5-dione; 1-benzyl-3-methylpyrazoline-4,5-dione; 1-benzyl-3-phenylpyrazoline-4,5-dione; 1-benzyl-3-(4'-methylphenyl)pyrazoline-4,5-dione; 1-benzyl-3-(3'-methoxyphenyl)pyrazoline-4,5-dione; 1-benzyl-3-(4'-methoxyphenyl)pyrazoline-4,5-dione; 1-benzyl-3-(3'-nitrophenyl)pyrazoline-4,5-dione; 1-benzyl-3-tert-butylpyrazoline-4,5-dione; 1-benzyl-3-methoxy-pyrazoline-4,5-dione; 1-benzyl-3-acetamidopyrazoline-4,5-dione; 1-benzyl-3-carboxypyrazoline-4,5-dione; 1-benzyl-3-methoxycarbonylpyrazoline-4,5-dione; 1-benzyl-3-(2'-furyl)pyrazoline-4,5-dione; 1-(4'-methoxyphenyl)pyrazoline-4,5-dione; 1-(4'-methoxyphenyl)-3-methylpyrazoline-4,5-dione; 1-(4'-methoxyphenyl)-3-(3'-methoxyphenyl)pyrazoline-4,5-dione; 1-(4'-methoxyphenyl)-3-phenylpyrazoline-4,5-dione; 1-(4'-methoxyphenyl)-3-(4'-chlorophenyl)-pyrazoline-4,5-dione; 1-(4'-methoxyphenyl)-3-(4'-methoxyphenyl)pyrazoline-4,5-dione; 1-(4'-methoxyphenyl)-3-(3'-nitrophenyl)pyrazoline-4,5-dione; 1-(4'-methoxyphenyl)-3-methoxypyrazoline-4,5-dione; 1-(4'-methoxyphenyl)-3-ethoxypyrazoline-4,5-dione; 1-(4'-methoxyphenyl)-3-acetamidopyrazoline-4,5-dione; 1-(4'-methoxyphenyl)-3-carboxypyrazoline-4,5-dione; 1-(4'-methoxyphenyl)-3-methoxycarbonyl-pyrazoline-4,5-dione; 3-(2'-furyl)-1-(4'-methoxyphenyl)pyrazoline-4,5-dione; 1-(4'-methoxyphenyl)-3-trifluoromethylpyrazoline-4,5-dione; 1-(4'-chlorophenyl)pyrazoline-4,5-dione; 1-(4'-chlorophenyl)-3-methylpyrazoline-4,5-dione; 1-(4'-chlorphenyl)-3-phenylpyrazoline-4,5-dione; 1-(4'-chlorophenyl)-3-(4'-methylphenyl)pyrazoline-4,5-dione; 1-(4'-chlorophenyl)-3-(3'-methoxyphenyl)-pyrazoline-4,5-dione; 1-(4'-chlorophenyl)-3-(4'-methoxyphenyl)pyrazoline-4,5-dione; 1-(4'-chlorophenyl)-3-(3'-nitrophenyl)pyrazoline-4,5-dione; 1-(4'-chlorophenyl)-3-methoxypyrazoline-4,5-dione; 1-(4'-chlorophenyl)-3-ethoxypyrazoline-4,5-dione; 1-(4'-chlorophenyl)-3-acetamidopyrazoline-4,5-dione; 1-(4'-chlorophenyl)-3-carboxypyrazoline-4,5-dione; 1-(4'-chlorophenyl)-3-methoxycarbonyl-pyrazoline-4,5-dione; 1-(4'-chlorophenyl)-3-(2'-furyl)-pyrazoline-4,5-dione; 1-(4'-chlorophenyl)-3-trifluoro-methylpyrazoline-4,5-dione; 1-(4'-nitrophenyl)pyrazoline-4,5-dione; 1-(4'-nitrophenyl)-3-methylpyrazoline-4,5-dione; 1-(4'-nitrophenyl)-3-phenylpyrazoline-4,5-dione; 1-(4'-nitrophenyl)-3-(4'-methylphenyl)pyrazoline-4,5-dione; 1-(4'-nitrophenyl)-3-(3'-methoxyphenyl)-pyrazoline-4,5-dione; 1-(4'-nitrophenyl)-3-(4'-methoxy-phenyl)pyrazoline-4,5-dione; 1-(4'-nitrophenyl)-3-(3'-nitrophenyl)pyrazoline-4,5-dione; 1-(40-nitrophenyl)-3-carboxypyrazoline-4,5-dione; 1-(4'-nitrophenyl)-3-(2'-furyl)pyrazoline-4,5-dione; 1-(4'-nitrophenyl)-3-trifluoromethylpyrazoline-4,5-dione; 3-trifluoromethylpyrazoline-4,5-dione; pyrazoline-4,5-dione; 3-methylpyrazoline-4,5-dione; 3-phenylpyrazoline-4,5-dione; 3-(4'-methylphenyl)-pyrazoline-4,5-dione; 3-(4'-methoxymethyl)pyrazoline-4,5-dione; 3-(4'-nitrophenyl)pyrazoline-4,5-dione; 3-methoxypyrazoline-4,5-dione; 3-acetamidopyrazoline-4,5-dione; 3-carboxypyrazoline-4,5-dione; 3-methoxycarbonylpyrazoline-4,5-dione; 3-(2'-furyl)pyrazoline-4,5-dione.

According to the present invention, it is most particularly preferred to use the pyrazoline-4,5-diones of formula (I) for which, cumulatively, $R_1$ is chosen from hydrogen or methyl, ethyl, n-propyl, isopropyl, tert-butyl and phenyl radicals and $R_2$ is chosen from hydrogen and methyl, phenyl, methoxyphenyl, methoxy, ethoxy, carboxyl, methoxycarbonyl, ethoxycarbonyl, acetamido, trifluoromethyl- and furyl radicals.

Thus, in the dye compositions according to the invention, it is more particularly preferred to use 3-methyl-1-phenylpyrazoline-4,5-dione; 3-methylpyrazoline-4,5-dione; 1,3-dimethylpyrazoline-4,5-dione; 1-ethyl-3-methylpyrazoline-4,5-dione; 1-isopropyl-3-methylpyrazoline-4,5-dione; 1-tert-butyl-3-methylpyrazoline-4,5-dione; 1-methyl-3-phenylpyrazoline-4,5-dione; 1-methyl-3-(3'-methoxyphenyl)pyrazoline-4,5-dione; 3-(2'-furyl)-1-methylpyrazoline-4,5-dione; 1-methyl-3-methoxypyrazoline-4,5-dione; 3-ethoxy-1-methylpyrazoline-4,5-dione; 3-diethylamino-1-methylpyrazoline-4,5-dione; 3-acetamido-1-methylpyrazoline-4,5-dione; 1-phenylpyrazoline-4,5-dione; 1-methylpyrazoline-4,5-dione; 1-ethylpyrazoline-4,5-dione; 1-isopropylpyrazoline-4,5-dione; 1-tert-butylpyrazoline-4,5-dione; 3-methoxy-1-phenylpyrazoline-4,5-dione; 3-ethoxy-1-phenylpyrazoline-4,5-dione; 3-acetamido-1-phenylpyrazoline-4,5-dione; 1-phenyl-3-trifluoromethyl-pyrazoline-4,5-dione; 1-methyl-3-trifluoromethyl-pyrazoline-4,5-dione; 1-isopropyl-3-trifluoromethyl-pyrazoline-4,5-dione; 1-ethyl-3-trifluoromethylpyrazoline-4,5-dione; 3-trifluoromethylpyrazoline-4,5-dione; 3-carboxy-1-phenylpyrazoline-4,5-dione; 3-methoxycarbonyl-1-phenylpyrazoline-4,5-dione; 3-ethoxycarbonyl-1-phenyl-pyrazoline-4,5-dione; 3-methoxypyrazoline-4,5-dione; 3-ethoxypyrazoline-4,5-dione; 3-carboxy-1-methylpyrazoline-4,5-dione; 3-methoxycarbonyl-1-methylpyrazoline-4,5-dione; 3-ethoxycarbonyl-1-methylpyrazoline-4,5-dione; 1-(n-propyl)pyrazoline-4,5-dione; 1-(n-propyl)-3-trifluoromethylpyrazoline-4,5-dione; 3-(2'-furyl)-1-(n-propyl)pyrazoline-4,5-dione; 3-(2'-furyl)-1-phenylpyrazoline-4,5-dione; 1-phenyl-3-tert-butylpyrazoline-4,5-dione; 1,3-diphenylpyrazoline-4,5-dione; 1-methyl-3-tert-butylpyrazoline-4,5-dione; 1-(n-propyl)-3-tert-butylpyrazoline-4,5-dione; 3-carboxy-1-methylpyrazoline-4,5-dione; 3-methoxycarbonyl-1-phenylpyrazoline-4,5-dione.

The pyrazoline-4,5-diones according to the invention can be prepared according to known processes comprising the following steps (the meanings of $R_1$ and $R_2$ are as given above).

The first process consists in:

a) reacting a pyrazolin-5-one ① with an aromatic nitroso compound ② so as to obtain the corresponding 4-aryliminopyrazolin-5-one ③:

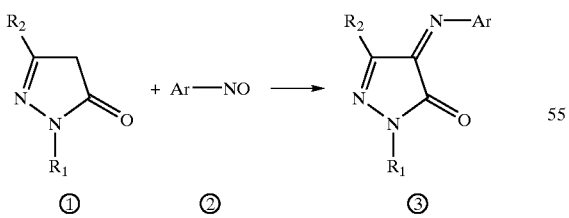

this reaction preferably being carried out in a lower alcohol such as methanol, ethanol or isopropanol, at a temperature of between 65° C. and 85° C., at the reflux point of the solvent used, and preferably in the presence of a weak base of carbonate or bicarbonate type, in catalytic amount, b) and then in hydrolysing the 4-aryliminopyrazolin-5-one ③, preferably in strong acid medium, to give the corresponding pyrazoline-4,5-dione derivative of formula (I):

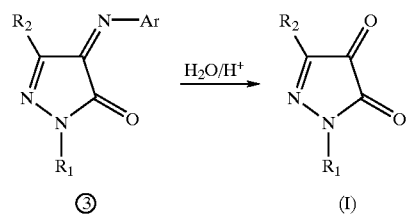

In such a process, the aromatic nitroso derivative of the first step is preferably a p-nitrosodialkylaniline of formula ②':

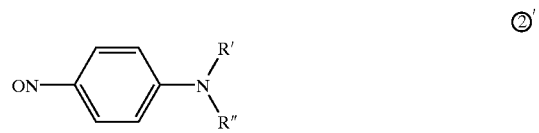

in which R' and R" represent a linear or branched $C_1$–$C_4$ alkyl radical.

The acid hydrolysis in the second step of the preparation process according to the invention is preferably carried out with dilute sulphuric acid or aqueous hydrochloric acid, at room temperature, in the presence of a co-solvent for the pyrazoline-4,5-dione which is immiscible with water, thus making it possible advanageously to extract the compound as it is formed, thereby making it easier to isolate in very high purity. The water-immiscible co-solvent can be a halogenated solvent such as, for example, dichloromethane or 1,2-dichloroethane. In one preferred embodiment of the invention, the water-immiscible co-solvent is an ether such as diethyl ether or diisopropyl ether.

The second process consists in:

a) reacting bromine with a pyrazolin-5-one of formula ① to give the corresponding 4,4-dibromopyrazolin-5-one of formula ④ (step a), b) and then in reacting lead diacetate so as to form the corresponding diacetate of formula ⑤, this being an unstable intermediate product which leads spontaneously, after elimination of acetic anhydride, to the desired pyrazoline-4,5-dione of formula (I) (step b), these two steps a and b thus being carried out according to the following reaction scheme:

Step a

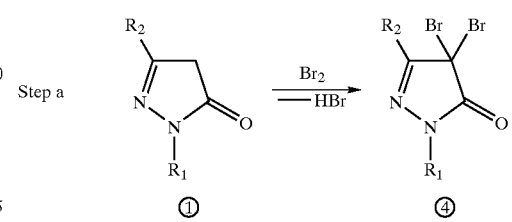

Step b 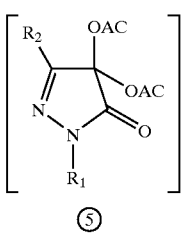

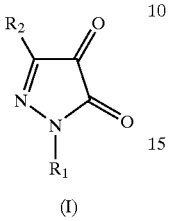
(I)

Step a of dibromination is preferably carried out in aqueous medium in the presence of two equivalents of bromine, at room temperature. The reaction is generally complete within a few hours: the dibromo derivative precipitates as it is formed, which allows simple isolation by filtration, in high purity.

Step b is advantageously carried out within a few hours at the reflux point of acetic acid, it being possible for the lead dibromide formed to be separated out very easily by simple filtration.

(ii) The aromatic or heteroaromatic amines which can be used according to the present invention are of formula (II) below:

$$R_9-NH_2 \quad (II)$$

in which $R_9$ represents:

- a 5- or 6-membered ring which can contain a maximum of 3 identical or different hetero atoms chosen from oxygen, nitrogen and sulphur,
- a set of 2 or 3 rings each being 5- or 6-membered, the set containing a maximum of 9 identical or different hetero atoms chosen from oxygen, nitrogen and sulphur, the said rings being fused or linked together via a hetero atom (O, N or S) or a polymethylene radical comprising from 1 to 5 carbon atoms, which may be linear or branched, saturated or unsaturated, and may contain, linked to or intercalated in the main chain, one or more oxygen, sulphur or nitrogen atoms, or sulphoxide, sulphone, disulphide, amino, $C_1$–$C_2$ alkylamino, hydroxyl, quaternary ammonium, ureido, amide or ester groups;

the ring(s) or heterocycle(s) denoted by $R_9$ can be unsubstituted or substituted with a maximum of 7 substituents chosen from amino, hydroxyl, cyano, trifluoromethyl, linear or branched $C_1$–$C_4$ alkyl, $C_1$–$C_4$ alkoxy, $C_1$–$C_4$ mono- or dialkylamino, carboxyl, $C_1$–$C_2$ alkoxycarbonyl, sulphonyl, sulphonamido, acetamido, amido, mercapto, $C_1$–$C_4$ alkylthio, nitro, $C_1$–$C_2$ alkylsulphone, $C_1$–$C_4$ hydroxyalkyl and keto radicals or a Cl, Br or F atom, and the cosmetically acceptable salts thereof.

The said aromatic or heteroaromatic amines are preferably chosen from anilines, aminoindoles, aminoisoindoles, aminobenzothiazoles, aminobenzimidazoles, aminobenzoxazoles, aminoquinolines, aminoisoquinolines, aminobenzoxazines, aminotetrahydroquinoxalines, aminobenzothiazines, aminotetrahydroisoquinolines, aminoindazoles, aminopyridines, aminopyrimidines, aminotriazines, aminonaphthalenes, aminopyrroles, aminopyrazoles, aminofurans, aminothiophenes, aminoimidazoles, aminooxazoles, aminothiazoles, aminoisoxazoles, aminoisothiazoles, aminotriazoles, aminouracils, aminothiouracils, aminojulolidines and aminopyrazolones.

Such amines are known per se, have been prepared in the prior art and are, in particular, the following:

para-phenylenediamine,
para-toluenediamine,
2-isopropyl-para-phenylenediamine
2-β-hydroxyethyl-para-phenylenediamine
2-β-hydroxyethyloxy-para-phenylenediamine
2,6-dimethyl-para-toluenediamine
2,6-diethyl-para-phenylenediamine
2,3-dimethyl-para-phenylenediamine
N,N-bis(2-hydroxyethyl)-para-phenylenediamine
4-amino-1-(2-methoxyethyl)-para-phenylenediamine
2-chloro-para-phenylenediamine,
para-aminophenol,
4-amino-3-methylphenol,
4-amino-3-fluorophenol,
4-amino-3-hydroxymethylphenol,
4-amino-2-methylphenol,
4-amino-2-hydroxymethylphenol,
4-amino-2-methoxymethylphenol,
4-amino-2-aminomethylphenol,
4-amino-2-(2-hydroxyethylaminomethyl)phenol,
2-aminophenol,
2-amino-1-hydroxy-5-methylbenzene,
2-amino-1-hydroxy-6-methylbenzene,
5-acetamido-2-aminophenol,
4,5-diamino-1,3-dimethylpyrazole,
4,5-diamino-1-ethyl-3-methylpyrazole,
4,5-diamino-1-n-propyl-3-methylpyrazole,
4,5-diamino-1-isopropyl-3-methylpyrazole,
3,4-diamino-5-methylpyrazole,
1-methyl-4,5-diaminopyrazole,
3,4-diaminopyrazole,
4,5-diamino-1-propylpyrazole,
4,5-diamino-1-methyl-3-tert-butylpyrazole,
9-aminojulolidine,
3,7-diaminopyrazolopyrimidine,
1,2-methylenedioxy-4-methoxy-5-aminobenzene,
2-methyl-3,5-diaminoindazole,
3,4-diamino-1,5-dimethylpyrazole.
4,5-diamino-1,3-dimethylisoxazole,
4,5-diamino-1,3-dimethylisothiazole,
4,5-diaminothiouracil,
4,5-diaminouracil,
2-(2-acetamidoethoxy)-1,4-diaminobenzene,
3-amino-1-(4-aminophenyl)pyrazoline,
4-amino-1-(4-aminophenyl)pyrazole,
2,3-diaminopyridine, and the cosmetically acceptable salts thereof.

For the purposes of the present invention, the cosmetically acceptable salts of the compounds of formula (I) and of the aromatic or heteroaromatic amines of formula (II) can be hydrochlorides, sulphates, hydrobromides or tartrates.

The concentration of pyrazoline-4,5-dione of formula (I) in the dye composition according to the present invention is preferably between about 0.01 and 5%, and even more preferably between about 0.15 and 2%, by weight relative to the total weight of the dye composition.

The concentration of aromatic or heteroaromatic amine in the dye composition according to the present invention is preferably between about 0.01 and 5%, and even more preferably between about 0.15 and 2%, by weight relative to the total weight of the dye composition.

The medium which is suitable for dyeing is preferably an aqueous medium consisting of water and/or cosmetically acceptable organic solvents, and more particularly alcohols such as ethyl alcohol, isopropyl alcohol, benzyl alcohol and phenylethyl alcohol, or glycols or glycol ethers such as, for example, ethylene glycol and its monomethyl, monoethyl and monobutyl ethers, propylene glycol or its ethers such as, for example, propylene glycol monomethyl ether, butylene glycol, dipropylene glycol and diethylene glycol alkyl ethers such as, for example, diethylene glycol monoethyl ether or monobutyl ether, in concentrations of between about 0.5 and 20%, and preferably between about 2 and 10%, by weight, relative to the total weight of the composition.

Fatty amides such as mono- and diethanolamides of acids derived from coconut, of lauric acid or of oleic acid, at concentrations of between about 0.05 and 10% by weight, can also be added to the dye composition according to the invention.

Surfactants that are well known in the prior art and of anionic, cationic, nonionic, amphoteric or zwitterionic type or mixtures thereof may also be added to the dye composition according to the invention, preferably in a proportion of between about 0.1 and 50% by weight and advantageously between about 1 and 20% by weight relative to the total weight of the composition.

Thickeners can also be used, in a proportion ranging from about 0.2 to 20%.

The said dye composition can also contain various common adjuvants such as antioxidants, fragrances, sequestering agents, dispersing agents, hair conditioning agents, preserving agents and opacifiers, as well as any other adjuvant usually used in the dyeing of keratin substances.

Needless to say, a person skilled in the art will take care to select the optional additional compound(s) mentioned above, such that the advantageous properties intrinsically associated with the dye composition according to the invention are not, or are not substantially, adversely affected by the addition(s) envisaged.

The dye composition according to the invention can be formulated at acidic, neutral or alkaline pH, it being possible for the pH to range, for example, from 2 to 12 and preferably from 3 to 9, and it being possible for it to be adjusted by means of basifying agents or acidifying agents or buffers which are previously well known.

Basifying agents which may be mentioned are aqueous ammonia, alkaline carbonates, alkanolamines, for example mono-, di- and triethanolamine and derivatives thereof, sodium hydroxide, potassium hydroxide and the compounds of formula:

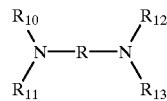

in which R is a propylene residue optionally substituted with a hydroxyl group or a $C_1$–$C_4$ alkyl radical; $R_{10}$, $R_{11}$, $R_{12}$ and $R_{13}$, simultaneously or independently, represent a hydrogen atom or a $C_1$–$C_4$ alkyl or $C_1$–$C_4$ hydroxyalkyl radical.

The acidifying agents are conventionally inorganic or organic acids such as, for example, hydrochloric acid, tartaric acid, citric acid and phosphoric acid.

Among the buffers which may be mentioned is, for example, potassium dihydrogen phosphate/sodium hydroxide.

The composition applied to the hair can be in various forms, such as in liquid, cream or gel form or in any other form which is suitable for dyeing keratin fibres. In particular, it can be packaged under pressure in an aerosol can, in the presence of a propellant and can form a mousse.

Another subject of the present invention relates to a process for dyeing keratin substances, in particular human keratin fibres such as the hair, this process consisting in applying a dye composition containing, in a medium which is suitable for dyeing, at least one pyrazoline-4,5-dione of formula (I) and an aromatic or heteroaromatic amine of formula (II) to wet or dry keratin fibres, in leaving the composition to act on the fibres for an exposure time ranging between 3 and 60 minutes approximately, preferably between 5 and 45 minutes approximately, at a temperature ranging between 20° C. and 50° C. approximately, and then in rinsing, optionally washing, rinsing again and drying.

One variant of the process constitutes another subject of the invention, and consists in applying to the keratin fibres, simultaneously or sequentially, (i) a dye composition containing, in a medium which is suitable for dyeing, at least one pyrazoline-4,5-dione of formula (I) and (ii) a composition essentially containing an aromatic or heteroaromatic amine of formula (II) in a medium which is suitable for dyeing.

Concrete examples illustrating the invention will now be given.

EXAMPLES OF DYE COMPOSITIONS

In Examples 1 to 4, the shades obtained on hair were assessed in numerical terms using a Minolta CM 2002 calorimeter.

The criterion of selectivity of the dyeing was evaluated by means of the colour variation index I, calculated according to the Nickerson equation below:

$$I=(C/5)\times 2\Delta H+6\Delta V+3\Delta C$$

(see in this respect "Journal of the Optical Society of America", September, 1944, Vol. 34, No. 9, pp. 550–570), in which equation, the parameters H, V and C represent those in the Munsell notation (ASTM standard D 1535–68), which defines colour [H: denoting the shade or Hue, V: denoting the intensity or Value, and C: denoting the purity or Chromaticity].

Example 1

The dye composition below, in accordance with the invention, was prepared immediately before use:

| | | |
|---|---|---|
| 3-Methyl-1-phenylpyrazoline-4,5-dione | 0.940 g | (0.005 mol) |
| para-Phenylenediamine | 0.540 g | (0.005 mol) |
| Ethyl alcohol | 40.0 g | |
| Citric acid | qs pH 2 | |
| Water | qs 100.0 g | |

The above composition was applied to locks of permanent-waved and non-permanent-waved natural grey hair containing 90% white hairs, at a rate of 6 g of composition per 3 g of hair, and was left to stand on the hair for 30 minutes at a temperature of about 20° C. After rinsing with running water, washing with a conventional shampoo, rinsing again and drying, the hair was dyed in a shade with a numerical value of 8.0 R 4.0/2.4 on non-permanent-waved hair and 6.4 R 3.4/3.1 on permanent-waved hair.

From this numerical Munsell data, the colour difference which exists between the permanent-waved hair and the non-permanent-waved hair was calculated (by means of the Nickerson equation). This difference, which represents the "selectivity" of the dyeing, was equal to 7.2.

Comparative Example 2

The dye composition below, according to the prior art, was prepared immediately before use:

| | | |
|---|---|---|
| Isatin (prior art dye) | 0.735 g | (0.005 mol) |
| para-Phenylenediamine | 0.540 g | (0.005 mol) |
| Ethyl alcohol | 40.0 g | |
| Citric acid | qs pH 2 | |
| Water | qs 100.0 g | |

The above composition was applied to locks of permanent-waved and non-permanent-waved natural grey hair containing 90% white hairs, according to the same procedure as in Example 1.

The hair was dyed in a shade with a numerical value of 6.9 YR 4.9/4.3 on non-permanent-waved hair and 3.6 YR 4.0/5.6 on permanent-waved hair.

From this numerical Munsell data, the colour difference which exists between the permanent-waved hair and the non-permanent-waved hair was calculated (by means of the Nickerson equation). This difference, which represents the "selectivity" of the dyeing, was equal to 15.0.

By comparison with the selectivity of the dyeing in Example 1 according to the invention, which was only 7.2, the selectivity of the dyeing in Example 2 (15.0) according to the prior art is much higher; it was thus demonstrated that permanent-waved hair comprising non-permanent-waved roots will show, after dyeing using composition 1 according to the invention, a more uniform (less selective) coloration than when using composition 2 of the prior art.

Example 3

The dye composition below, in accordance with the invention, was prepared immediately before use:

| | | |
|---|---|---|
| 3-Methyl-1-phenylpyrazoline-4,5-dione | 0.940 g | (0.005 mol) |
| 2-β-Hydroxyethyl-para-phenylene-diamine dihydrochloride | 1.120 g | (0.005 mol) |
| Ethyl alcohol | 40.0 g | |
| Citric acid | qs pH 2 | |
| Water | qs 100.0 g | |

The above composition was applied to locks of permanent-waved and non-permanent-waved natural grey hair containing 90% white hairs, according to the same procedure as in Example 1.

The hair was dyed in a shade with a numerical value of 4.9 R 3.6/2.3 on non-permanent-waved hair and 2.7 R 3.0/2.9 on permanent-waved hair.

From this numerical Munsell data, the colour difference which exists between the permanent-waved hair and the non-permanent-waved hair was calculated (by means of the Nickerson equation). This difference, which represents the "selectivity" of the dyeing, was equal to 7.4.

Comparative Example 4

The dye composition below, according to the prior art, was prepared immediately before use:

| | | |
|---|---|---|
| Isatin (prior art dye) | 0.735 g | (0.005 mol) |
| 2-β-Hydroxyethyl-para-phenylene-diamine dihydrochloride | 1.120 g | (0.005 mol) |
| Ethyl alcohol | 40.0 g | |
| Citric acid | qs pH 2 | |
| Water | qs 100.0 g | |

The above composition was applied to locks of permanent-waved and non-permanent-waved natural grey hair containing 90% white hairs, according to the same procedure as in Example 1.

The hair was dyed in a shade with a numerical value of 5.6 YR 4.4/3.3 on non-permanent-waved hair and 0.9 YR 3.4/4.9 on permanent-waved hair.

From this numerical Munsell data, the colour difference which exists between the permanent-waved hair and the non-permanent-waved hair was calculated (by means of the Nickerson equation). This difference, which represents the "selectivity" of the dyeing, was equal to 17.0.

By comparison with the selectivity of the dyeing in Example 3 according to the invention, which was only 7.4, the selectivity of the dyeing in Example 4 (17.0) according to the prior art is much higher; it was thus demonstrated that permanent-waved hair comprising non-permanent-waved roots will show, after dyeing using composition 3 according to the invention, a more uniform (less selective) coloration than when using composition 4 of the prior art.

Example 5

The dye composition below, in accordance with the invention, was prepared immediately before use:

| | | |
|---|---|---|
| 3-Methyl-1-phenylpyrazoline-4,5-dione | 0.94 g | (0.005 mol) |
| 4,5-Diamino-1-methyl-3-tert-butylpyrazole dihydrochloride | 1.21 g | (0.005 mol) |

-continued

| Hydroxypropyl guar sold under the name Jaguar HP-60 by the company Mayhall | 1.00 g | |
| --- | --- | --- |
| Alkyl (50/50 $C_8/C_{10}$) polyglucoside (2) as a 60% aqueous solution, sold under the name Oramix CG110 by the company SEPPIC | 5.00 g | AM* |
| Ethyl alcohol | 10.00 g | |
| Preserving agents | qs | |
| Monoethanolamine | qs | pH 6 |
| Demineralized water | qs | 100.0 g |

AM* = active material

The above composition was applied to locks of permanent-waved and non-permanent-waved natural grey hair containing 90% white hairs, at a rate of 6 g of composition per 3 g of hair, and was left to stand on the hair for 30 minutes at a temperature of about 20° C. After rinsing with running water, washing with a conventional shampoo, rinsing again and drying, the hair was dyed in a coppery-iridescent shade on non-permanent-waved hair and a red-coppery shade on permanent-waved hair.

Example 6

The dye composition below, in accordance with the invention, was prepared immediately before use:

| 3-Methyl-1-phenylpyrazoline-4,5-dione | 0.94 g | (0.005 mol) | |
| --- | --- | --- | --- |
| 3,7-Diaminopyrazolopyrimidine dihydrochloride | 1.11 g | (0.005 mol) | |
| Hydroxypropyl guar sold under the name Jaguar HP-60 by the company Mayhall | 1.00 g | | |
| Alkyl (50/50 $C_8/C_{10}$) polyglucoside (2) as a 60% aqueous solution, sold under the name Oramix CG110 by the company SEPPIC | 5.00 g | | AM* |
| Ethyl alcohol | 10.00 g | | |
| Preserving agents | qs | | |
| Monoethanolamine | qs | pH 4 | |
| Demineralized water | qs | 100.0 g | |

The above composition was applied to locks of permanent-waved and non-permanent-waved natural grey hair containing 90% white hairs, at a rate of 6 g of composition per 39 of hair, and was left to stand on the hair for 30 minutes at a temperature of about 50° C. After rinsing with running water, washing with a conventional shampoo, rinsing again and drying, the hair was dyed in an intense red-coppery shade on non-permanent-waved hair and a strong coppery-red shade on permanent-waved hair.

Example 7

The dye composition below, in accordance with the invention, was prepared immediately before use:

| 3-Methyl-1-phenylpyrazoline-4,5-dione | 0.94 g | (0.005 mol) |
| --- | --- | --- |
| 2-(2-Acetamidoethoxy)-1,4-diaminobenzene dihydrochloride | 1.41 g | (0.005 mol) |
| Hydroxypropyl guar sold under | 1.00 g | |

-continued

| the name Jaguar HP-60 by the company Mayhall | | |
| --- | --- | --- |
| Alkyl (50/50 $C_8/C_{10}$) polyglucoside (2) as a 60% aqueous solution, sold under the name Oramix CG110 by the company SEPPIC | 5.00 g | AM* |
| Ethyl alcohol | 10.00 g | |
| Preserving agents | qs | |
| Monoethanolamine | qs | pH 6 |
| Demineralized water | qs | 100.0 g |

The above composition was applied to locks of permanent-waved and non-permanent-waved natural grey hair containing 90% white hairs, at a rate of 6 g of composition per 3 g of hair, and was left to stand on the hair for 30 minutes at a temperature of about 50° C. After rinsing with running water, washing with a conventional shampoo, rinsing again and drying, the hair was dyed in an intense purple-red shade on non-permanent-waved hair and on permanent-waved hair.

Example 8

The dye composition below, in accordance with the invention, was prepared immediately before use:

| 1-Methyl-3-tert-butyl-pyrazoline-4,5-dione | 0.84 g | (0.005 mol) | |
| --- | --- | --- | --- |
| para-Phenylenediamine | 0.54 g | (0.005 mol) | |
| Hydroxypropyl guar sold under the name Jaguar HP-60 by the company Mayhall | 1.00 g | | |
| Alkyl (50/50 $C_8/C_{10}$) polyglucoside (2) as a 60% aqueous solution, sold under the name Oramix CG110 by the company SEPPIC | 5.00 g | | AM* |
| Ethyl alcohol | 10.00 g | | |
| Preserving agents | qs | | |
| Monoethanolamine | qs | pH 6 | |
| Demineralized water | qs | 100.0 g | |

The above composition was applied to locks of permanent-waved and non-permanent-waved natural grey hair containing 90% white hairs, at a rate of 6 g of composition per 3 g of hair, and was left to stand on the hair for 30 minutes at a temperature of about 50° C. After rinsing with running water, washing with a conventional shampoo, rinsing again and drying, the hair was dyed in a coppery-iridescent shade on non-permanent-waved hair and on permanent-waved hair.

Example 9

The dye composition below, in accordance with the invention, was prepared immediately before use:

| 1-Methyl-3-phenylpyrazoline 4,5-dione | 0.94 g | (0.005 mol) |
| --- | --- | --- |
| para-Phenylenediamine | 0.54 g | (0.005 mol) |
| Hydroxypropyl guar sold under the name Jaguar HP-60 by the company Mayhall | 1.00 g | |
| Alkyl (50/50 $C_8/C_{10}$) polyglucoside (2) as a 60% aqueous | 5.00 g | AM* |

-continued

| | | |
|---|---|---|
| solution, sold under the name Oramix CG110 by the company SEPPIC | | |
| Ethyl alcohol | 10.00 g | |
| Preserving agents | qs | |
| Monoethanolamine | qs | pH 6 |
| Demineralized water | qs | 100.0 g |

The above composition was applied to locks of permanent-waved and non-permanent-waved natural grey hair containing 90% white hairs, at a rate of 6 g of composition per 3 g of hair, and was left to stand on the hair for 30 minutes at a temperature of about 50° C. After rinsing with running water, washing with a conventional shampoo, rinsing again and drying, the hair was dyed in a deep iridescent-violet shade on non-permanent-waved hair and on permanent-waved hair.

Example 10

The dye composition below, in accordance with the invention, was prepared immediately before use:

| | | |
|---|---|---|
| 1,3-Diphenylpyrazoline 4,5-dione | 1.25 g | (0.005 mol) |
| para-Phenylenediamine | 0.54 g | (0.005 mol) |
| Hydroxypropyl guar sold under the name Jaguar HP-60 by the company Mayhall | 1.00 g | |
| Alkyl (50/50 $C_8/C_{10}$) poly-glucoside (2) as a 60% aqueous solution, sold under the name Oramix CG110 by the company SEPPIC | 5.00 g | AM* |
| Ethyl alcohol | 10.00 g | |
| Preserving agents | qs | |
| Monoethanolamine | qs | pH 9 |
| Demineralized water | qs | 100.0 g |

The above composition was applied to locks of permanent-waved and non-permanent-waved natural grey hair containing 90% white hairs, at a rate of 6 g of composition per 3 g of hair, and was left to stand on the hair for 30 minutes at a temperature of about 50° C. After rinsing with running water, washing with a conventional shampoo, rinsing again and drying, the hair was dyed in an ash-golden shade on non-permanent-waved hair and a slightly coppery-golden shade on permanent-waved hair.

What is claimed is:
1. A composition for dyeing keratin fibers comprising:
   (i) at least one pyrazoline-4,5-dione of formula (I), below, or a cosmetically acceptable salt thereof,

(I)

in which:
$R_1$ is chosen from:
    a hydrogen atom;
    linear and branched $C_1$–$C_6$ alkyl radicals optionally substituted with a radical chosen from —OH, —COOH, $C_1$–$C_4$ alkoxy, $C_1$–$C_4$ hydroxyalkyl, and $C_1$–$C_4$ dialkylamino;
    a radical $$-(CH_2)_m-O-(CH_2)_n-R_4,$$
$$\qquad\qquad\qquad |$$
$$\qquad\qquad\qquad R_3$$

wherein m is 1, 2, or 3; n is 1, 2, or 3; $R_3$ is chosen from hydrogen and methyl; and $R_4$ is chosen from methyl, hydroxyl, linear and branched $C_1$–$C_5$ alkoxy radicals, and linear and branched $C_1$–$C_5$ hydroxyalkyl radicals;
    a radical $-(CH_2)_p-O-R_5$, wherein p is 1 or 2, and $R_5$ is chosen from substituted and unsubstituted phenyl radicals;
    a radical $-(CH_2)_q-R_6$, wherein q is 1 or 2, and $R_6$ is chosen from thienyl, furyl, pyridyl, piperidyl, and phenyl radicals, said phenyl radicals being optionally substituted with a maximum of 2 groups chosen from methyl, trifluoromethyl, sulphonyl, and methoxy radicals;
    phenyl radicals which are optionally substituted with one to five groups chosen from: —COOH, —CH$_2$COOH, —NO$_2$, —OH, —SO$_3$H, —CH$_2$OH, —OCF$_3$, —CF$_3$, —SO$_2$CH$_3$, —SO$_2$NH$_2$, —SO$_2$NHC$_2$H$_5$, —SO$_2$NHCH$_2$CH$_2$OH, —CON(CH$_3$)$_2$, —CON(C$_2$H$_5$)$_2$, —CH$_2$N(CH$_3$)$_2$, —CH$_2$N(C$_2$H$_5$)$_2$, —NHCOCH$_3$, —NHCOC$_2$H$_5$, halogens, linear and branched $C_1$–$C_3$ alkyl radicals, and a radical —Z—$R_7$, wherein Z is chosen from O and S, and $R_7$ is chosen from a hydrogen atom, and linear and branched $C_1$–$C_3$ alkyl radicals;
    benzyl radicals which are optionally substituted with a radical chosen from —COOH, —OCH$_3$, and —SO$_3$H; and
    pyridyl, pyrimidinyl, pyrazinyl, thiazinyl, benzothiazolyl, benzimidazolyl, thienyl, imidazolyl, thiazolyl, 1,2,4-triazolyl, indazolyl, indolyl, quinolyl, and isoquinolyl radicals;
and $R_2$ is chosen from:
    a hydrogen atom;
    linear and branched $C_1$–$C_6$ alkyl radicals optionally substituted with a group chosen from hydroxyl and $c_1$–$C_4$ alkoxy radicals;
    phenyl radicals which are optionally substituted with a radical chosen from halogens, nitro, and trifluoromethyl,
    phenyl radicals substituted with a maximum of 3 radicals chosen from $C_1$–$C_4$ alkyl, $C_1$–$C_4$ alkoxy, $C_1$–$C_4$ dialkylamino, and $C_1$–$C_2$ alkylthio;
    a radical $-(CH_2)_r-R_8$ in which r is 1, 2, or 3, and $R_8$ is chosen from —SO$_3$H, $C_1$–$C_2$ alkylthio, benzylthio, methoxycarbonyl, ethoxycarbonyl, and phenyl radicals, said phenyl radicals being optionally substituted with a radical chosen from halogens, $C_1$–$C_3$ alkyl, $C_1$–$C_3$ alkoxy, $C_1$–$C_4$ dialkylamino, and $C_1$–$C_2$ alkylthio;
    $C_1$–$C_4$ alkoxy radicals;
    phenoxy radicals optionally substituted with at least one halogen atom; and
    trifluoromethyl, acetamido, $C_1$–$C_2$ dialkylamino, carboxyl, methoxycarbonyl, ethoxycarbonyl, thienyl, furyl, pyridyl, and pyrazolyl radicals;
it being understood that when $R_2$ is chosen from alkyl and phenyl radicals, $R_2$ can be linked to the carbon atom of the pyrazoline ring via a hetero atom chosen from O, N and S;

and, (ii) at least one aromatic or heteroaromatic amine of formula (II), below, or a cosmetically acceptable salt thereof:

 (II)

in which:
R₉ is chosen from:
5- and 6-membered rings optionally containing a maximum of 3 identical or different hetero atoms chosen from oxygen, nitrogen, and sulphur; and sets of 2 and 3 rings, wherein each set of rings contains a maximum of 9 identical or different hetero atoms chosen from oxygen, nitrogen, and sulphur, and each ring is 5- or 6-membered and is fused or linked together via a group chosen from O, N, S, and linear and branched, saturated and unsaturated, polymethylene radicals comprising from 1 to 5 carbon atoms, said polymethylene radicals optionally containing, linked to or intercalated in the main chain, at least one group chosen from oxygen, sulphur, nitrogen, sulphoxide, sulphone, disulphide, amino, $C_1$–$C_2$ alkylamino, hydroxyl, quaternary ammonium, ureido, amide, and ester radicals,
wherein said R₉ rings and sets of rings are optionally substituted with a maximum of 7 substituents chosen from amino, hydroxyl, cyano, trifluoromethyl, linear and branched $C_1$–$C_4$ alkyl, $C_1$–$C_4$ alkoxy, $C_1$–$C_4$ mono- and dialkylamino, carboxyl, $C_1$–$C_2$ alkoxycarbonyl, sulphonyl, sulphonamido, acetamido, amido, mercapto, $C_1$–$C_4$ alkylthio, nitro, $C_1$–$C_2$ alkylsulphone, $C_1$–$C_4$ hydroxyalkyl, and keto radicals, and Cl, Br, and F atoms.

2. A dye composition according to claim 1, wherein said at least one pyrazoline-4,5-dione is chosen from
(i) compounds of formula (I) for which R₁ is chosen from:
a hydrogen atom,
linear and branched $C_1$–$C_4$ alkyl radicals optionally substituted with a radical chosen from —OH and $C_1$–$C_2$ alkoxy;
a radical —(CH₂)_q-R₆, in which q is 1 or 2, and R₆ is chosen from phenyl radicals optionally substituted with a group chosen from methyl, trifluoromethyl, and sulphonyl radicals; and
phenyl radicals optionally substituted with a radical chosen from $C_1$–$C_2$ alkyl, $C_1$–$C_2$ alkoxy, —SO₃H, —COOH, —OH, —CF₃, —NO₂, and halogens; and
(ii) compounds of formula (I) for which R₂ is chosen from:
a hydrogen atom,
linear and branched $C_1$–$C_4$ alkyl radicals optionally substituted with a radical chosen from hydroxyl and $C_1$–$C_2$ alkoxy;
phenyl radicals optionally substituted with a radical chosen from halogens, $C_1$–$C_4$ alkyl, $C_1$–$C_2$ alkoxy, and $C_1$–$C_2$ dialkylamino; and
$C_1$–$C_3$ alkoxy, trifluoromethyl, acetamido, $C_1$–$C_2$ dialkylamino, carboxyl, methoxycarbonyl, ethoxycarbonyl, furyl, thienyl, pyridyl, and pyrazolyl radicals.

3. A dye composition according to claim 1, wherein said at least one pyrazoline-4,5-dione is chosen from compounds of formula (I) for which R₁ is chosen from hydrogen, methyl, ethyl, n-propyl, isopropyl, tert-butyl, and phenyl radicals, and R₂ is chosen from hydrogen, methyl, phenyl, methoxyphenyl, methoxy, ethoxy, carboxyl, methoxycarbonyl, ethoxycarbonyl, acetamido, trifluoromethyl, and furyl radicals.

4. A dye composition according to claim 1, wherein said at least one pyrazoline-4,5-dione is chosen from: 3-methyl-1-phenyl-pyrazoline-4,5-dione; 3-methylpyrazoline-4,5-dione; 1,3-dimethylpyrazoline-4,5-dione; 1-ethyl-3-methylpyrazoline-4,5-dione; 1-isopropyl-3-methylpyrazoline-4,5-dione; 1-tert-butyl-3-methylpyrazoline-4,5-dione; 1-methyl-3-phenylpyrazoline-4,5-dione; 1-methyl-3-(3'-methoxyphenyl)pyrazoline-4,5-dione; 3-(2'-furyl)-1-methylpyrazoline-4,5-dione; 1-methyl-3-methoxypyrazoline-4,5-dione; 3-ethoxy-1-methylpyrazoline-4,5-dione; 3-diethylamino-1-methylpyrazoline-4,5-dione; 3-acetamido-1-methylpyrazoline-4,5-dione; 1-phenylpyrazoline-4,5-dione; 1-methylpyrazoline-4,5-dione; 1-ethylpyrazoline-4,5-dione; 1-isopropylpyrazoline-4,5-dione; 1-tert-butylpyrazoline-4,5-dione; 3-methoxy-1-phenylpyrazoline-4,5-dione; 3-ethoxy-1-phenylpyrazoline-4,5-dione; 3-acetamido-1-phenylpyrazoline-4,5-dione; 1-phenyl-3-trifluoromethylpyrazoline-4,5-dione; 1-methyl-3-trifluoromethylpyrazoline-4,5-dione; 1-isopropyl-3-trifluoromethylpyrazoline-4,5-dione; 1-ethyl-3-trifluoromethylpyrazoline-4,5-dione; 3-trifluoromethylpyrazoline-4,5-dione; 3-carboxy-1-phenylpyrazoline-4,5-dione; 3-methoxycarbonyl-1-phenylpyrazoline-4,5-dione; 3-ethoxycarbonyl-1-phenylpyrazoline-4,5-dione; 3-methoxypyrazoline-4,5-dione; -,4,5-dione; 3-carboxy-1-methylpyrazoline-4,5-dione; 3-methoxycarbonyl-1-methylpyrazoline-4,5-dione; 3-ethoxycarbonyl-1-methylpyrazoline-4,5-dione; 1-(n-propyl)pyrazoline-4,5-dione; 1-(n-propyl)-3-trifluoromethylpyrazoline-4,5-dione; 3-(2'-furyl)-1-(n-propyl)pyrazoline-4,5-dione; 3-(2'-furyl)-1-phenylpyrazoline-4,5-dione; 1-phenyl-3-tert-butylpyrazoline-4,5-dione; 1,3-diphenylpyrazoline-4,5-dione; 1-methyl-3-tert-butylpyrazoline-4,5-dione; 1-(n-propyl)-3-tert-butylpyrazoline-4,5-dione; 3-carboxy-1-methylpyrazoline-4,5-dione; 3-methoxycarbonyl-1-phenylpyrazoline-4,5-dione; and the cosmetically acceptable salts thereof.

5. A dye composition according to claim 1, wherein said at least one aromatic or heteroaromatic amine is chosen from: anilines, aminoindoles, aminoisoindoles, aminobenzothiazoles, aminobenzimidazoles, aminobenzoxazoles, aminoquinolines, aminoisoquinolines, aminobenzoxazines, aminotetrahydroquinoxalines, aminobenzothiazines, aminotetrahydroisoquinolines, aminoindazoles, aminopyridines, aminopyrimidines, aminotriazines, aminonaphthalenes, aminopyrroles, aminopyrazoles, aminofurans, aminothiophenes, aminoimidazoles, aminooxazoles, aminothiazoles, aminoisoxazoles, aminoisothiazoles, aminotriazoles, aminouracils, aminothiouracils, aminojulolidines and aminopyrazolones.

6. A dye composition according to claim 5, wherein said at least one aromatic or heteroaromatic amine is chosen from: para-phenylenediamine; para-toluenediamine; 2-isopropyl-para-phenylenediamine; 2-β3-hydroxyethyl-para-phenylenediamine; 2-β-hydroxyethyloxy-para-phenylenediamine; 2,6-dimethyl-para-toluenediamine; 2,6-diethyl-para-phenylenediamine; 2,3-dimethyl-para-phenylenediamine; N,N-bis(2-hydroxyethyl)-para-phenylenediamine; 4-amino-1-(2-methoxyethyl) aminobenzene; 2-chloro-para-phenylenediamine; para-aminophenol; 4-amino-3-methylphenol; 4-amino-3-fluorophenol; 4-amino-3-hydroxymethylphenol; 4-amino-2- methylphenol; 4-amino-2-hydroxymethylphenol; 4-amino-2-methoxymethylphenol; 4-amino-2-aminomethylphenol; 4-amino-2-(2-hydroxyethylaminomethyl)phenol; 2-aminophenol; 2-amino-1-hydroxy-5-methylbenzene; 2-amino-1-hydroxy-6-methylbenzene; 5-acetamido-2-aminophenol; 4,5-diamino-1,3-dimethylpyrazole; 4,5-diamino-1-isopropyl-3-methylpyrazole; 4,5-diamino-1-ethyl-3-methylpyrazole; 4,5-diamino-1-n-propyl-3-methylpyrazole; 3,4-diamino-5-methylpyrazole; 1-methyl-4,5-diaminopyrazole; 3,4-diaminopyrazole; 4,5-diamino-1-propylpyrazole; 4,5-diamino-1-methyl-3-tert-butylpyrazole; 9-aminojulolidine; 3,7-diaminopyrazolopyrimidine; 1,2-methylenedioxy-4-methoxy-5-aminobenzene; 2-methyl-3,5-diaminoindazole; 3,4-diamino-1,5-dimethylpyrazole; 4,5-diamino-1,3-dimethylisoxazole; 4,5-diamino-1,3-dimethylisothiazole; 4,5-diaminothiouracil; 4,5-diaminouracil; 2-(2-acetamidoethoxy)-1,4-diaminobenzene; 3-amino-1-(4-aminophenyl)pyrazoline; 4-amino-1-(4-aminophenyl)pyrazole; 2,3-diaminopyridine; and the cosmetically acceptable salts thereof.

7. A dye composition according to claim 1, wherein said composition has a pH ranging from 2 to 12.

8. A dye composition according to claim 1, further comprising a medium suitable for dyeing, wherein said medium is chosen from water and organic solvents chosen from alcohols, glycols and glycol ethers, and wherein said organic solvents are present in said composition in an amount ranging from 0.5 to 20% by weight relative to the total weight of the composition.

9. A dye composition according to claim 1, wherein said halogens are chosen from Cl, Br, and F.

* * * * *